(12) United States Patent
Labat et al.

(10) Patent No.: US 6,313,342 B1
(45) Date of Patent: *Nov. 6, 2001

(54) SYNTHESIS OF ESTERS OF MERCAPTOCARBOXYLIC ACIDS

(75) Inventors: Yves Labat; Jean-Pierre Muller, both of Pau (FR)

(73) Assignee: Elf Atochem S.A., Puteaux (FR)

( * ) Notice: Subject to any disclaimer, the term of this patent is extended or adjusted under 35 U.S.C. 154(b) by 0 days.

This patent is subject to a terminal disclaimer.

(21) Appl. No.: 09/567,087

(22) Filed: May 8, 2000

Related U.S. Application Data

(60) Continuation of application No. 09/063,399, filed on Apr. 21, 1998, now abandoned, which is a division of application No. 08/516,699, filed on Aug. 18, 1995, now Pat. No. 5,773,641.

(30) Foreign Application Priority Data

Aug. 19, 1994 (FR) .................................. 94 10145

(51) Int. Cl.⁷ ................................................ C07C 319/12
(52) U.S. Cl. .............................................. 560/147
(58) Field of Search ................................ 560/147

(56) References Cited

U.S. PATENT DOCUMENTS

| | | | |
|---|---|---|---|
| 2,262,686 | 11/1941 | Kyrides et al. | 260/481 |
| 3,927,085 | 12/1975 | Zengel et al. | 560/152 |
| 5,773,641 * | 6/1998 | Labat et al. | 560/147 |

OTHER PUBLICATIONS

R.M. Acheson et al., "The Synthesis of Some Thiophens Related to . . . ", *J.C.S.*, pp. 650–660, 1961.
Translation Of Chemical Abstract, JP 63–10755, published Jan. 18, 1988.
Translation of Chemical Abstract, Abstract No. 59499z, vol. 80(11), JP–48–86818, published Nov. 15, 1973.
Acheson et al.. "The Synthesis of Some Thioplens Related to Vitamin A", J.C.S. 1161 (pp. 650–660), 1961.
Translation of JP 48–86818. 1973.
Translation of JP 63–10755. 1988.

* cited by examiner

*Primary Examiner*—Samuel Barts
(74) *Attorney, Agent, or Firm*—Millen, White, Zelano & Branigan, P.C.

(57) ABSTRACT

Esters of formula:

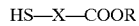

in which X denotes a $C_1$–$C_4$ alkylene radical and R a $C_1$–$C_{18}$ alkyl radical, are prepared by reaction of a hydrosulphide with the corresponding halocarboxylic ester:

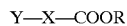

where Y denotes a chlorine or bromine atom. The reaction is performed under a hydrogen sulphide pressure of at least 10 bars absolute, and preferably in an anhydrous or substantially anhydrous alcoholic medium.

7 Claims, No Drawings

SYNTHESIS OF ESTERS OF MERCAPTOCARBOXYLIC ACIDS

This application is a continuation of U.S. application Ser. No. 09/063,399, filed Apr. 21, 1998 now abondoned, which is a divisional of Ser. No. 08/516,699, filed Aug. 18, 1995 now U.S. Pat. No. 5,773,641 both of which applications are incorporated by reference herein in their entirety.

The present invention relates to the preparation of esters of mercaptocarboxylic acids and more particularly to the synthesis of esters of the general formula:

HS—X—COOR     (I)

in which X denotes a linear or branched alkylene radical containing from 1 to 4 carbon atoms and R a linear or branched alkyl radical containing from 1 to 18 carbon atoms, preferably 1 to 12.

BACKGROUND OF THE INVENTION

These known esters are used industrially as intermediate products, especially for the manufacture of tin derivatives which are useful as heat stabilizers for polyvinyl chloride and, in the case of the lower alcohol esters (especially R=methyl), for the manufacture of heterocyclic (thiophene or thiazole) derivatives which are useful as plant-protection agents.

The main route for obtaining esters (I) is the esterification of an alcohol ROH with an acid HS—X—COOH, the latter being obtained by the action of a hydrosulphide on the corresponding chloro- or bromocarboxylic acid. Despite its excellent overall yield, this method has the disadvantage of generating a considerable quantity of aqueous saline waste.

It is known that esters of mercaptocarboxylic acids can also be prepared by the action of an alkali metal hydrosulphide on an ester of a halocarboxylic acid. This method has been employed especially by R. M. Acheson et al. (J. Chem. Soc. 1961, pp. 650–660, in particular p. 656) for preparing methyl α-mercapto-α-methylpropionate by the action of sodium hydrosulphide on methyl α-bromo-α-methylpropionate in anhydrous methanol; the yield is very low (approximately 36%). Additional systems are described in Patent Applications JP 48-86818, 63-10755 and 2-304061, both of which operate in the presence of water, either in a hydroalcoholic medium (JP 48-86818 and 63-10755) or in a water-toluene medium in the presence of a phase transfer agent (JP 2-304061).

It has now been found that the presence, in the reaction medium, of appreciable quantities of water (other than that possibly originating from the in-situ formation of the hydrosulphide) is unfavorable for the selectivity of the reaction and that this selectivity is moreover improved by operating at a high pressure of hydrogen sulphide.

SUMMARY OF THE INVENTION

An object of this invention is therefore to provide one or more improved processes for the preparation of the esters of formula (I) by the action of ammonium hydrosulphide or of an alkali or alkaline-earth metal hydrosulphide on the corresponding halocarboxylic ester of formula:

Y—X—COOR     (II)

in which R and X have the same meanings as above and Y denotes a chlorine or bromine atom.

Upon further study of the specification and appended claims, further objects and advantages of this invention will become apparent to those skilled in the art.

To obtain these objects, the reaction is performed under a hydrogen sulphide pressure of at least 10 bars absolute, and preferably in an anhydrous or substantially anhydrous alcoholic medium.

The expression "substantially anhydrous" means here that the reaction medium does not contain water in amounts other than that which may originate from the possible in-situ formation of hydrosulphide, as is the case, for example, with the formation of sodium hydrosulphide according to the reaction:

$$NaOH + H_2S \rightarrow NaSH + H_2O$$

A $C_1$–$C_4$ lower alcohol may be employed as alcohol, but it is preferred to work in isopropanol and especially in methanol. Although it is preferred to employ an anhydrous or substantially anhydrous alcoholic medium, the benefits of such a medium are still obtained to a finite extent even though the water content of the medium is as high as 36 g per liter of alcohol used to form the medium.

The reaction may be performed at a temperature ranging from 0 to 80° C., but it is preferred to operate at a temperature of between 10 and 60° C.

The hydrogen sulphide pressure may range up to preferably not more than 30 bars absolute, but is advantageously between 10 and 20 bars absolute. The use of such hydrogen sulphide pressures contribute to improved selectivities, even in media which are not anhydrous or substantially anhydrous.

Although the process according to the invention also applies to bromocarboxylic esters, it is preferred to start from chlorocarboxylic esters, obtained in excellent yields (approximately 96%) according to the esterification reaction:

$$Cl—X—COOH + ROH \rightarrow Cl—X—COOR + H_2O$$

Depending on the nature of the ester (II) used, its initial concentration in the reaction medium may preferably range from 1 to 5 moles per liter of alcohol.

An alkali or alkaline-earth metal hydrosulphide such as, for example, NaSH, RSH and $Ca(SH)_2$ may be employed as the hydrosulphide, but it is preferred to employ ammonium hydrosulphide, which can be formed in situ without producing water. The hydrosulphide/ester (II) molar ratio is generally between 1 and 2 but, in order to obtain a complete conversion of the ester (II), it preferably ranges from 1.1 to 1.5. The values indicated for this ratio should obviously be halved when a difunctional hydrosulphide such as $Ca(SH)_2$ is employed.

The process according to the invention may be used continuously or discontinuously (batchwise). When compared with the usual process of preparation of esters of mercaptocarboxylic acids by esterification of an alcohol ROH with an acid HS—X—COOH, it offers the advantage, on the one hand, of forming as a by-product approximately half as much ammonium salt or alkali or alkaline-earth metal salt, and on the other hand, of considerably reducing the quantity of saline aqueous waste. In fact, after neutralization of the excess hydrosulphide in the reaction mixture with an acid (preferably HCl or $H_2SO_4$), the precipitated salts can be easily separated off by filtration, before or after evaporation of the alcohol.

Without further elaboration, it is believed that one skilled in the art can, using the preceding description, utilize the present invention to its fullest extent. The following preferred specific embodiments, are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight, and the pressures of $H_2O$ in bars absolute.

The entire disclosures of all applications, patents and publications, cited above and below, and of corresponding French Application No. P 94/10145, are hereby incorporated by reference.

EXAMPLE 1

151 g of a methanolic solution of ammonia at a concentration of 9.1% (that is 0.808 mol of $NH_3$) were charged into a stainless steel autoclave and then hydrogen sulphide was introduced up to a pressure of 12 bars absolute. 120 g (0.57 mol) of 2-ethylhexyl chloroacetate were then introduced over 40 minutes with the aid of a pump while the temperature was maintained at 10±2° C. The reactants were agitated for one hour and the autoclave was then decompressed.

Analysis of the methanolic solution showed that it contained 49.3% of 2-ethylhexyl thioglycolate and 1.2% of 2-ethylhexyl thiodiglycolate, that is a yield of 97.4 % of 2-ethylhexyl thioglycolate.

After neutralization with the aid of hydrochloric acid, the methanolic solution was heated under vacuum to evaporate the methanol and then filtered to separate off the precipitated ammonium chloride, and finally distilled. A 2-ethylhexyl thioglycolate of purity greater than 99% and free from residual acidity was thus collected.

EXAMPLE 2

350 g of a methanolic solution of sodium hydrosulphide at a concentration of 8.5% (that is 0.53 mol of NaSH) were charged into the same reactor as in Example 1 and the pressure was then raised to 10 bars by introducing hydrogen sulphide.

39 g (0.36 mol) of methyl chloroacetate were then introduced while the temperature was maintained at 10° C.

After the reaction and a return to atmospheric pressure, a methanolic solution was obtained, containing:

8.7% of methyl thioglycolate
0.96% of methyl thiodiglycolate
<0.01% of methyl chloroacetate which corresponds to a yield of 89% of methyl thioglycolate.

EXAMPLES 3 TO 9

Using the same operating process as in Examples 1 and 2, seven tests for the preparation of 2-ethylhexyl thioglycolate were carried out by varying the $H_2S$ pressure, the temperature and/or the hydrosulphide/2-ethylhexyl chloroacetate molar ratio.

In Examples 3 and 4, which are given by way of comparison, all (Example 3) or half (Example 4) of the methanol was replaced with water.

The operating conditions and the results obtained are summarized in the following table, where R denotes the radical $—CH_2COOC_8H_{17}$.

| EXAMPLE | Hydrosulphide | $H_2S$ pressure (bars) | Temperature (° C.) | Hydrosulphide/RCl molar ratio | RCl conversion (%) | Yields (%) of compound: | | | |
|---|---|---|---|---|---|---|---|---|---|
| | | | | | | RSH | R-S-R | R-SS-R | ROH |
| 3[a] comparative | $NH_4SH$ | 1 | 40 | 1.5 | 39.5 | 14.3 | 15.4 | 9.1 | 0.7 |
| 4[b] comparative | $NH_4SH$ | 15 | 25–35 | 1.1 | 99.99 | 80 | 10 | 5[c] | 5 |
| 5 | $NH_4SH$ | 12 | 40 | 1.1 | 100 | 91 | 8.4 | 0 | 0.6 |
| 6 | $NH_4SH$ | 13 | 18 | 1.1 | 100 | 94 | 5.6 | 0 | 0.4 |
| 7 | $NH_4SH$ | 8 | 18 | 1.1 | 100 | 86 | 13.6 | 0 | 0.4 |
| comparative 8 | NaSH | 1 | 40 | 2 | 100 | 42 | 50.1 | 6.8 | 1.1 |
| comparative 9 | NaSH | 10 | 10 | 1.1 | 100 | 93 | 6.2 | 0 | 0.8 |

[a]Test performed in water
[b]Test performed in a 50/50 mixture of water and methanol
[c]Including a little thioglycolic acid and methyl thioglycolate The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a process for the preparation of an ester of mercaptocarboxylic acid of formula:

$$HS—X—COOR \quad (I)$$

in which X denotes a linear or branched alkylene radical containing from 1 to 4 carbon atoms and R a linear or branched alkyl radical containing from 1 to 18 carbon atoms, comprising reacting ammonium hydrosulphide or an alkali or alkaline-earth metal hydrosulphide with the corresponding halocarboxylic ester of formula:

$$Y—X—COOR \quad (II)$$

in which R and X have the same meanings as above and Y denotes a chlorine or bromine atom, the improvement comprising conducting the reaction under a hydrogen sulphide pressure of at least 10 bars absolute and at a temperature from 10 to 40° C.

2. A process according to claim 1, in which the hydrogen sulphide pressure is between 10 and 20 bars absolute.

3. A process according to claim 1, in which the hydrosulphide/ester (II) molar ratio is between 1 and 2.

4. A process according to claim 1, in which ammonium hydrosulphide is employed.

5. A process according to claim 1, in which the hydrosulphide/ester (II) molar ratio is between 1.1 and 1.5.

6. A process according to claim 1, wherein the medium is anhydrous.

7. A process according to claim 6, in which the alcohol is methanol or isopropanol.

* * * * *